United States Patent [19]

MacCoss et al.

[11] Patent Number: 4,801,710
[45] Date of Patent: Jan. 31, 1989

[54] REGIOSELECTIVE SYNTHESIS OF 9-SUBSTITUTED PURINE ACYCLONUCLEOSIDE DERIVATIVES

[75] Inventors: Malcolm MacCoss, Freehold; Richard L. Tolman, Warren; Arthur F. Wagner, Princeton; John Hannah, Matawan, all of N.J.

[73] Assignee: Merck & Co., Inc., Rahway, N.J.

[21] Appl. No.: 153,539

[22] Filed: Feb. 2, 1988

Related U.S. Application Data

[63] Continuation of Ser. No. 665,409, Oct. 26, 1984, abandoned.

[51] Int. Cl.$^4$ .................. C07D 473/18; A61K 31/52
[52] U.S. Cl. .................................. 544/244; 544/276; 544/277
[58] Field of Search .................. 544/276, 277, 244

[56] References Cited

U.S. PATENT DOCUMENTS

4,495,190 1/1985 Hagberg et al. .................. 544/276
4,579,849 4/1986 MacCoss et al. .................. 544/276

OTHER PUBLICATIONS

Ogilvie et al., Can J. Chem., vol. 60, 3005–3010 (1962).
Martin et al., J. Med. Chem. (1983), vol. 26, No. 5, pp. 759–761.
Lee et al., Jour of Org Chemistry, vol. 37, pp. 2923–2927 (1972).

Primary Examiner—Nicholas S. Rizzo
Attorney, Agent, or Firm—Richard S. Parr; Hesna J. Pfeiffer

[57] ABSTRACT

A process for preparing 9-substituted guanine-containing acyclonucleosides comprising selective alkylation at the 9-position of the purine by utilizing a blocking group at the 6-position.

8 Claims, No Drawings

REGIOSELECTIVE SYNTHESIS OF 9-SUBSTITUTED PURINE ACYCLONUCLEOSIDE DERIVATIVES

This is a continuation of application Ser. No. 665,409 filed Oct. 26, 1984, now abandoned.

BACKGROUND OF THE INVENTION

The present invention relates to regioselective synthesis of acyclonucleosides and their derivatives.

Guanine-related acyclonucleosides with the purine substitution at the 9-position have been recognized as potentially important antiviral agents. Unfortunately, it was difficult to prepare such compounds without alkylation (glycosylation) occurring at the 7-position as well; for example, see Ogilivie et al., *Can. J. Chem.*, 60, 3005–3010 (1982) and Martin et al., *J. Med. Chem.*, 26, 759–61 (1983) for 7/9 mixtures which are generally difficult to separate.

We have discovered a novel process for preparing 9-substituted guanine-related acyclonucleosides which prevents or minimizes alkylation at the 7-position and which furnishes 7- and 9- isomers which are much more easily separated. This method is also generally applicable to other purines. The word "alkylation" is used here to refer to attachment of an alkyl or cycloalkyl substituent containing protected or unprotected hydrophilic groups, where the carbon at the attachment site can be an alkyl carbon or else a carbon at the aldehyde oxidation state, such as an acetal or aminal carbon. The words "guanine-related" shall be understood to mean 2,6-disubstituted purines where the 2- and 6-subtitutuents are amino or protected amino and hydroxy or protected hydroxy, respectively, and groups which can be converted to the aforementioned groups by nucleophilic substitution, for example, displacement of halide ion from 2-amino-6-choropurine. Thus, "guanine-related" includes compounds such as 2-amino-6-benzyloxypurine; 2,6-dichloropurine; 2-bromohypoxanthine; 2,6 diazidopurine;-2,6-dichloropurine; 2-acetamido-6-chloropurine; 2-acetamidohypoxanthine; and 2-isobutyramidohypoxanthine.

The process of the present invention comprises alkylation of pro-guanine derivatives having a bulky and hydrophobic blocking group at the 6-position of the purine and optionally at the 2-position of the purine. When appropriate in the synthesis, the blocking group (or groups) may be removed by standard methods (for example, by hydrogenolysis or treatment with acid, e.g. dilute hydrochloric acid, dilute sulfuric acid or trifluoroacetic acid, or by nucleophilic placement, followed by hydrolysis or β-elimination). The words "pro-guanine derivative" shall be understood to mean a purine derivative which can be converted by deprotection or nucleophilic substitution to guanine or a 9-substituted guanine derivative such as 2-amino- 6- benxyloxypurine or 2-chloro-6-benzyloxypurine or 2-isobutylamido-6-(p-nitrophenylethoxy)purine.

Any blocking group that will effectively prevent or minimize alkylation at the 7-position may be used in the 6-position of the pro-guanine derivative. Examples of suitable blocking groups are 6-benzyloxy, substituted 6-benzyloxy, 6-phenoxy, substituted 6-phenoxy, 6-(2-phenylethoxy), substituted 6-(2-phenylethoxy), especially 6-[2-(4-nitrophenyl)ethoxy]; aryl- and substituted arylsulfonyloxy, and 6-(aryl-and/or alkyl-siloxy); and 6-(β-cyanoethoxy). As used herein aryl means phenyl, naphthyl, substituted phenyl or substituted naphthyl. The aforementioned benzyloxy, phenoxy, phenylethoxy, aryl and phenyl groups may be substituted on the phenyl or naphthyl moieties with substituents selected from $C_1$ to $C_6$ alkyl, halo (i.e., fluoro, chloro, bromo and iodo), nitro, phenyl, and trifluoromethyl.

The pro-guanine derivative is alkylated with a suitable alkylating agent in an inert solvent at a temperature of $-80°$ to $150°$ depending on the reactivity of the alkylating agent and the nature of the solvent. Atmospheric pressure is preferred but higher or lower pressures may be used, if desired. Alkylation may also be accomplished in the presence of a strong base such as sodium hydride, potassium carbonate, triethylamine, or lithium diisopropylethylamide.

Optionally the pro-guanine heterocyclic derivative may be trimethylsilylated to facilitate solution and increase yields.

The following reaction schemes illustrate the process of the present invention:

Scheme Ia

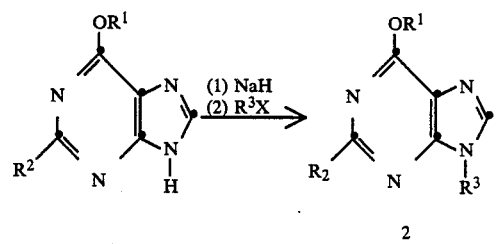

X=halogen, tosylate, acetate, or other appropriate leaving group
$R^1$=blocking group
$R^2$=NH$_2$, Cl, Br
$R^3$=protected, side-chain derivative Scheme Ib

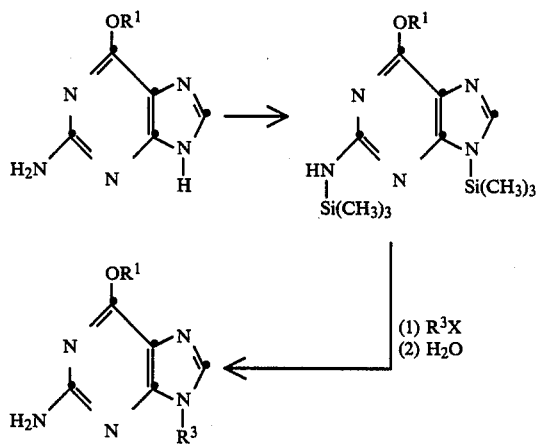

As showm in Scheme II, the process of the present invention may be used to prepare (S)-9-(2,3-dihydroxy-1propoxymethyl)guanine:

Scheme II

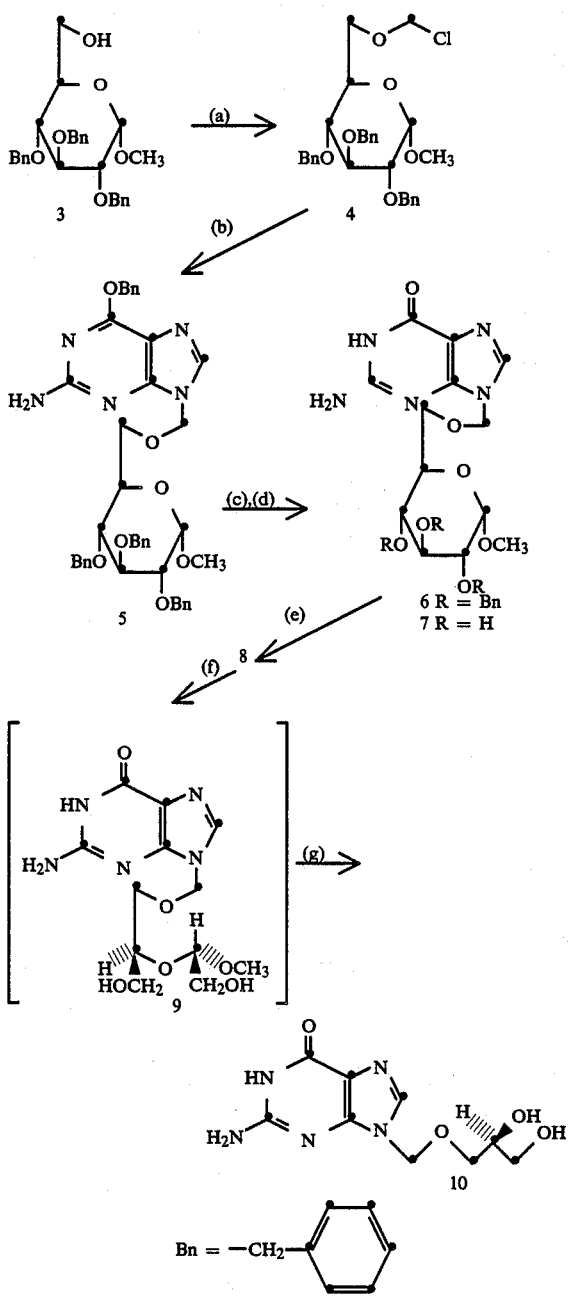

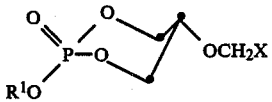

(a) CH₂O, HCl (g), CH₂Cl₂, 0°
(b) 2-amino-6-benzyloxypurine, NaH, DMF, room temperature
(c) 20% Pd (OH)₂ on carbon, H₂ (50 psi), EtOH
(d) 20% Pd (OH)₂ on carbon, H₂ (50 psi), TsOH, EtOH/H₂O
(e) NaIO₄ in H₂O
(f) NaBH₄
(g) HAc-HCl (20:3 v/v), 55°-60°, 1½ hours, or CF₃CO₂H: H₂O 1:9, room temperature, overnight.

Methyl 2,3,4-tri-O-benzyl-α-D-glucopyranoside is prepared in two steps from the commercially available methyl α-D-glucopyranoside; see R. Eby and C. Schuerch, Carbohydrate Res. 34, 79 (1974). The compound was chloromethylated at the 6-position using paraformaldehyde and HCl gas in CH₂Cl₂ as solvent. (Caution: Bis-chloromethyl ether, a potent carcinogen, is presumably formed as a by-product in this reaction and the procedure should be carried out in a well ventilated hood). The product, methyl 2,3,4-tri-O-benzyl-6-O-chloromethyl-α-D-glucopyranoside, is used to alkylate 2-amino-6-benzyloxypurine. The product, methyl 2,3,4-tri-O-benzyl-6-O-(2-amino-6-benzyloxypurin-9-ylmethyl)-α-D-glucopyranoside, is obtained after a silica gel column separation. Debenzylation is carried out by hydrogenation over 20% Pd(OH)₂ on carbon. In this deblocking step, the presence or absence of p-toluenesulfonic acid determines the nature of the product formed. Thus, when the acid is omitted, debenzylation of the heterocycle occurs leaving the blocking groups on the sugar moiety intact. In this way, the intermediate may be readily isolated. If 3 molar equivalents of p-toluenesulfonic acid are added to the hydrogenation, complete deblocking occurs to give methyl 6-O-(guanin-9-ylmethyl)-α-D-glucopyranoside.

The methyl 6-O-(guanin-9-ylmethyl)-α-D-glycopyranoside, is dissolved in water and treated with sodium periodate (3 molar equivalents). After removal of excess periodate by precipitation with strontium chloride, the intermediate dialdehyde 8 is not isolated but rs reduced immediately with sodium borohydride to give the presumed (2S,1'S)-2-O(2'-hydroxy-1'-methoxyethyl)-1-O-(guanin-9-ylmethyl) glycerol 9. Acidic hydrolysis of 9 with HAc-HCl or with aqueous CF₃COOH gives the required 10.

Other compounds that may be prepared by the process of the present invention are cyclic phosphates of 2,6-substituted purines.

Acyclonucleoside cyclic phosphates are disclosed in European patent application No. 82401571.3, publication No. 0 074 306, U.S. Ser. No. 538,019, filed Sept. 30, 1983 and U.S. Ser. No. 616,910, filed June 6, 1984. These compounds were prepared by direct phosphorylation of an acyclonucleoside which contained two hydroxyl groups. Yields were poor because in solvent systems where the acyclonucleosides had measurable solubility, phosphorylation of the second hydroxyl was able to compete successfully with the cyclization reaction of the first phosohorylation. Using the process of the present invention, a phosphorylated side chain is separately synthesized and this side chain is used to alkylate a suitably substituted purine or pyrimidine.

Thus, in one of its embodiments the present invention relates to a process for preparing cyclic phosphates of 2,6-substituted purines comprising alkylating a purine having a blocking group at the 6-position with a compound of the formula:

$$\text{R}^1\text{O}-\overset{\overset{\displaystyle O}{\|}}{\underset{|}{P}}-O\diagdown\diagup OCH_2X$$

wherein
R¹ is alkyl of 1 to 18 carbons, haloalkyl of 1 to 18 carbon atoms, benzyl, substituted benzyl, phenyl or substituted phenyl, wherein halo means fluorine, chlorine, bromine or iodine and the substituents on the phenyl group or the phenyl moiety of the benzyl group are selected from alkyl, nitro and halogen; and X is a suitable leaving group.

Preferably X is halide (i.e., fluorine, chlorine, bromine or iodine) or tosyloxy;

More preferably X is chloride.

Preferably, $R^1$ is o-chlorophenyl.

Preferred pro-guanine derivatives are 2-amino-6-benzyloxypurine, 2-chloro-6-benzyloxypurine, 2-amino-6-o-nitrophenoxypurine, 2-amino-6-[2-(4-nitrophenyl)ethoxy]purine, 2-amino-6-β-cyanoethoxypurine, 2-amino-6-chloropurine, and 2,6-dichloropurine. Most preferably the pro-guanine derivative is 2-amino-6-benzyloxypurine.

A preferred embodiment of the present invention relates to a process for preparing a compound of the formula:

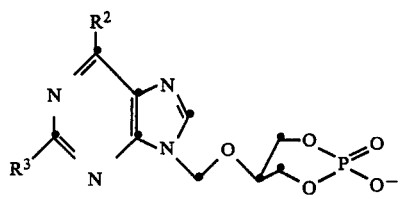

wherein
 $R^2$ is benzyloxy; and
 $R^3$ is amino;
comprising alkylating a compound of the formula:

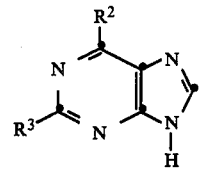

wherein $R^2$ and $R^3$ are as defined above with a compound of the formula:

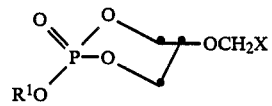

wherein $R^1$ is as defined above and X is a suitable leaving group. Preferably X is halide or tosyloxy. More preferably, X is chloride.

The following reaction scheme illustrates this process.

Scheme III

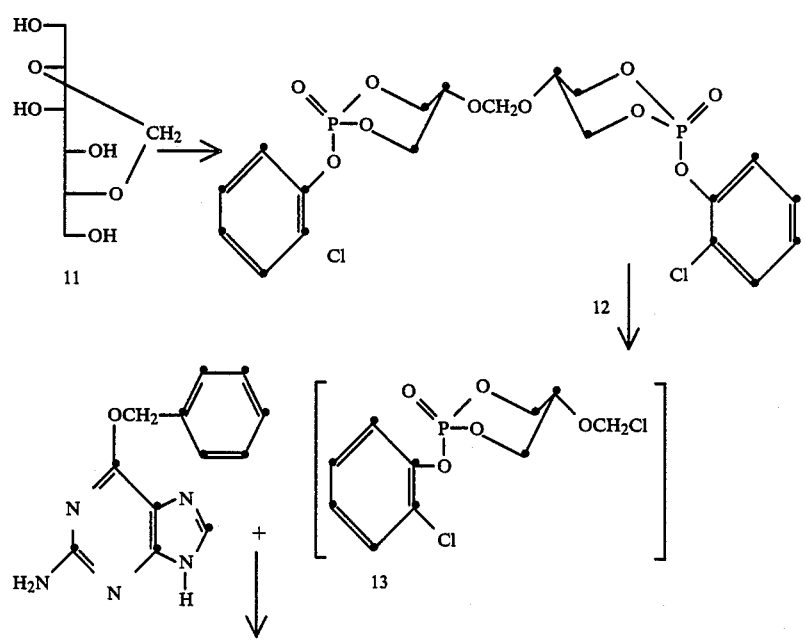

Scheme III

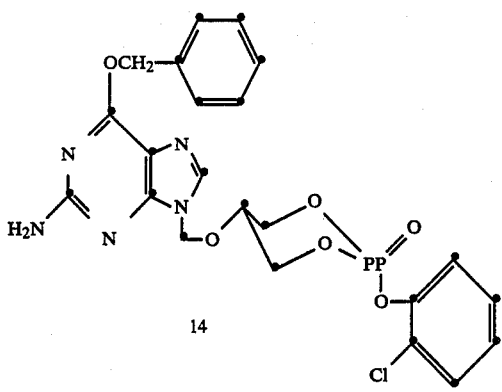

14

2,5-Methylene-D-mannitol (11) is converted by a multi-step procedure to the Bis-protected-1,3,2-dioxaphosphorinan-5-yloxy P-oxide derivative (12) which is converted by formaldehyde and hydrogen chloride to the reactive chloromethyl ether derivative 13. Alkylation by 13 of the pro-guanine derivative, 2-amino-6-benzyloxy-purine, either as the silyl derivative in an inert solvent such as acetonitrile, tetrahydrofuran, benzene or toluene or directly in the presence of a strong base such as sodium hydride in dimethylformamide, gives predominantly the 9-substituted product 14 which can be deprotected at the 6-position by hydrogenolysis and-/or aqueous acid treatment.

The following examples illustrate the processes of the present invention. All temperatures are in degrees Celsius.

EXAMPLE 1

2-Amino-6-benzyloxypurine

Step 1: 2-Aminopurin-6-yltrimethylammonium chloride[a]

2-Amino-6-chloropurine (70 g, 0.41 mol) was dissolved (with warming to 70°) in sieve-dried DMF (dimethylformamide) (3L). The solution was cooled to −5° and eight 100 mL portions of condensed liquid trimethylamine were added. After the addition was complete, the reaction was stirred (temp. 0°) for 1½ hours and then allowed to rise to room temperature overnight. The white solid of 2-aminopurin-6-yltrimethylammonium chloride was filtered off and washed with acetone and ethyl ether to yield 87.3 g (92.5%). A second crop gave an additional 4.5 g (total yield: 91.8 g, 97.3%).

[a] Preparation first described in J. Chem. Soc. (C) 3942 (1971).

Step 2 2-Amino-6-benzyloxypurine[b]

26.8 g (1.17 mol) of sodium spheres and benzyl alcohol (335 mL. 3.24 mol) were mixed and stirred under $N_2$. An exothermic reaction was apparent and the mixture was cooled with an ice-bath. After controlling the reaction, the mixture was heated to 125° to complete the formation of sodium benzyloxide and was then cooled to room temperature 132.7 g (0.58 mol) of 2-aminopurin-6-yltrimethylammonium chloride, as a suspension in sieve-dried DMSO (dimethylsulfoxide) (550 mL), was then added and the temperature rose to 35°. The reaction was stirred at room temperature for 2 hours TLC (thin layer chromatography) on silica developed with ethyl acetate-ethanol, 4:1 showed complete reaction after 1 hour) and then was poured into a mixture of ice (1160 g) and 1N HCl (1160 mL). Additional 1N HCl was added to bring the pH to 1 and then the mixture was extracted three times with ethyl ether. The aqueous phase was filtered and brought to pH 8 (with stirring) by the careful addition of solid $NaHCO_3$. A precipitate formed which was filtered off after stirring 1 hour. The solid was washed with $H_2O$ and air-dried overnight to give 128.5 g (92.7%) of the title compound.

[b] Other published procedures for the synthesis of the title compound are available: J. Org. Chem., 34, 2160 (1969); J. Med. Chem. 6, 471 (1963).

EXAMPLE 2

Preparation of o-chlorophenoxy-2-oxo-1,3,2-dioxaphosphorinan-5-ylchloromethyl ether Step 1: Methylene-bis-2-glycerol 350 g(1.80 mol) of 2,5-methylene-D-mannitol[a] (8) was dissolved in HO (4375 mL) and cooled, with stirring to 4°. $NaIO_4$ (424.4 g; 1.98 mol); n $H_2O$ (2800 mL) was added at a rate which kept the temperature below 15°. The ice-bath was removed and the reaction was allowed to rise to room temperature. After 2 hours the reaction was cooled in an ice-bath and $BaCl_2.2H_2O$ (253.8 g) was added in portions. The solid so formed was filtered off and washed with cold $H_2O$ after standing at 0° for 2¼, hours. To the filtrate (about 9L) was added 9 tablespoons of Raney Nickel and the mixture was agitated at 2000 psi (136 atmospheres) of $H_2$ at room temperature in a bomb for 18 hours. The bomb was rinsed with $H_2O$ (2X4L) and the catalyst was filtered off and washed with $H_2O$. The filtrate and washings were evaporated to dryness to give a gummy, semicrystalline residue which was dried in vacuo for 2 days. This residue was treated with boiling ethanol and then the mixture was filtered (washing the solid well with hot ethanol). The filtrate was evaporated to dryness and the residue so obtained was dissolved in boiling ethanol (690 mL) and then cooled. Crystallization occurred and the solid was filtered, washed with cold ethanol and ethyl ether, yielding 237.8 g, m.p. 85°–86°. A second crop gave 64.5 g, m.p. 83°–85°, for a total yield of 302.3 g (85.5%).

[a] Prepared from D-mannitol in 3 steps by literature procedure (Ness, Hann and Hudson, JACS, 65, 2215 (1943)).

Step 2:
Di-(2-o-chlorophenoxy-1,3,2-dioxaphosphorinan-5-yloxy)methane bis-P-oxide (11)

A mixture of sieve-dried toluene (225 mL) and sieve-dried pyridine (225 mL) were stirred and cooled (ice-bath) under $N_2$. Methylene-bis-2-glycerol (50 g; 0.255 mol) in sieve-dried pyridine (1500 mL) was added dropwise to the solution simultaneously as a solution of o-chlorophenyl phosphorodichloridate (86.5 mL; 128.97 g; 0.525 mol) in sieve-dried toluene (1500 mL) was added-keeping the addition of the methylene-bis-2-glycerol slightly faster (i.e., always in excess). The addition took place over 80 minutes, while maintaining the temperature below 10°. After addition was complete, the ice-bath was removed and the reaction was stirred at room temperature overnight under $N_2$. The reaction mixture was filtered and the solid was washed well with toluene. The filtrate and washings were then evaporated to a syrup in vacuo. This residue was dissolved in $CH_2Cl_2$, washed 3 times with saturated aqueous $NaHCO_3$ and the organic phase was dried over $MgSO_4$, filtered and evaporated to dryness. The residue was dried in vacuo for 2 days to yield 142.6 g (quantitative). TLC examination (silica, developed in ethyl acetate) showed 2 spots.[a] This material was used directly in the next step.

[a] Identical preparations showed that these 2 spots were the 3 expected isomers (NMR and mass spectrometry analysis)—one isomer is isolatable (the faster-moving spot) and the remaining 2 isomers migrate together in this solvent system (slower-moving spot).

Step 3:
o-Chlorophenoxy-2-oxo-1,3,2-dioxaphosphorinan-5-yl chloromethyl ether[b]

The foregoing 142.6 g of the title compound of Example 3, Step 2 (presumably 0.255 mol and trace impurity), was dissolved in $CH_2Cl_2$ (2500 mL) and paraformaldehyde (9.7 g; 0.32 mol) was added. This mixture was stirred and cooled to −5° (ice-methanol bath) and HCl (g) was bubbled through the mixture for 2½ hours. A clear solution quickly formed. The stoppered reaction was allowed to rise to room temperature slowly and was stirred for 72 hours. NMR on an aliquot indicated complete reaction and $MgSO_4$ was added to the reaction mixture.[c] After stirring for a short time the mixture was filtered through a pad of $MgSO_4$ and the filtrate was concentrated in vacuo. The residue was redissolved in $CH_2Cl_2$ and some insolubles were filtered off. This filtrate was evaporated to dryness, azeotroped two times from dry toluene and the residue was then dried in vacuo for 18 hours. The syrup so formed weighed 145.1 g (91% yield) and NMR indicated the expected 2 isomers (about a 1:1 ratio).

[b] Care, bis-chloromethyl ether formed as by-product.
[c] Dry $N_2$ was usually bubbled through the mixture at this point to remove as much of the chloromethyl ether as possible before concentration.

EXAMPLE 3

Preparation of 2-Amino-6-benzyloxy-9-[(o-chlorophenoxy-1,3,2-dioxaphosphorinan-5-yl)oxy)methyl]purine P-oxide

Method A 124.4 g (0.52 mol) of the compound from Example 1 (2-amino-6-benzyloxy-purine) in dry DMF (285 mL) was stirred under $N_2$ while 25.5 g (0.64 mol of NaH) of NaH (60% in oil) was added in portions. The temperature rose to 45°–50° with vigorous evolution of $H_2$. The reaction was cooled to room temperature (cold-bath) and stirred for 30 minutes (a clear brown solution was formed). A freshly prepared solution of the title compound of Example 2 (145.1 g, 0.46 mol) in dry DMF (dimethylformamide) (285 mL) was added from a dropping funnel and a slight exotherm was observed—the temperature was maintained at about 20°–25° using a cold bath. The reaction mixture became cloudy and after 3½ hours TLC (silica, 5% methanol in ethyl acetate) showed some unreacted purine derivative and a portion (about 0.1 mol) of NaH was added. After a total of 6½ hours reaction time the mixture was filtered and the solid was well washed with $CH_2Cl_2$. The filtrate was evaporated to dryness in vacuo to give a reddish-brown syrup. This residue was dissolved in $CH_2Cl_2$ and washed with aqueous saturated NaHCO (Note: emulsions were formed and the layers were allowed to stand until complete separation had occurred). The organic phase was dried, filtered and evaporated to dryness in vacuo to give a red foam (276.8 g). This residue was suspended in $CH_2Cl_2$ and the solid was removed by filtration (16.0 g of unreacted purine derivative). The filtrate was applied to an EM (E. Merck) silica gel column (15.0×52.5 cm) packed in $CH_2Cl_2$. After an initial volume of $CH_2Cl_2$, the column was developed with ethyl acetate. The trans isomer of the title compound was obtained (36.5 g) as well as the cis isomer (2.5 g) as well as easily separated $N^7$ isomers in smaller amounts. The pure trans and cis isomers could be crystallized to give analytically pure material, but were used without crystallization in the subsequent deblocking steps.

Method B 85.5 g (0.35 mol) of 2-amino-6-benzyloxypurine (Example 1) and ammonium sulfate (14.5 g, 0.11 mol) were mixed and hexamethyldisilazane (1830 mL) was added. This mixture was stirred and heated at reflux under $N_2$ for 2 hours. Essentially complete solution was obtained and the reaction was filtered to remove ammonium sulfate, washing with toluene. The filtrate was evaporated to dryness in vacuo and the residue was evaporated 2 more times from dry toluene. This residual syrup was then dissolved in dry toluene (610 mL) and $Hg(CN)_2$ (97.6 g, 0.39 mol) was added. The mixture was refluxed for 15 minutes under $N_2$ and then 115 g (0.37 mol) of freshly prepared title compound of Example 2 in dry toluene (153 mL) was added from a dropping funnel. The reflux was continued for 3 hours at which point TLC (silica, developed in ethyl acetate) showed some unreacted purine derivative. An additional 48.5 g (0.155 mol) of title compound of Example 2 in dry toluene (300 mL) was added and after a further 1½ hours the reaction was cooled and evaporated to dryness. The residue was stirred at room temp. under $CH_2Cl_2$ (4L) for 60 hours and then was filtered (washing the pad with $CH_2Cl_2$). The filtrate was concentrated to about 3L and then extracted with 30% aqueous KI solution (3×1.3 L), 10% aqueous $K_2CO_3$ solution (3×1.3 L) and saturated aqueous NaCl (1×1.3 L). The organic phase was dried over $Na_2SO_4$, filtered and evaporated in vacuo to a gum (117.2 g). This was dissolved in $CH_2Cl_2$ and applied to an EM silica gel column (3.68 kilo) packed in $CH_2Cl_2$. After washing-on with $CH_2Cl_2$, the column was developed with ethyl acetate. This gave 21.1 g of slightly contaminated trans title compound and 1.9 g of slightly contaminated cis title compound. In addition, 4.9 g of pure cis title compound was obtained along with 4.7 g of unreacted purine starting material derivative, 2.4 g of N7-trans title compound isomer and 13 g of a mixture of the purine starting material derivative and the N7-trans title compound.

EXAMPLE 4

2-Amino-9-[(2)-2-(benzoyloxymethyl)cyclobutylmethyl]-6-benzoyloxypurine

To a stirred solution of 907 mg (3.76 mmole) of 2-amino-6-benzyloxypurine in 10 ml of dry DMF was added 166 mg (4.14 mmole) of sodium hydride (60% dispersion in oil). The mixture was stirred under nitrogen at ambient temperature. After 30 minutes, by which time a homogeneous solution had been obtained, a solution of 1.55 g (4.14 mmole) of (Z)-1-benzoyloxymethyl-2-(p-toluenesulfonyloxymethyl)cyclobutane in 1.0 ml of DMF was added dropwise. The mixture was stirred under nitrogen at 60° C. for 12 hours. At this time, thin layer chromatography (TLC) in ethyl acetate showed a strong uv-absorbing product spot ($R_f$ about 0.7) along with a weak spot at the origin. There was no evidence of isomers. The mixture was neutralized with glacial acetic acid and then concentrated in vacuo (less than 5 mm Hg). The residue was taken up in ethyl acetate, filtered, and chromatographed on a silica gel column (elution with ethyl acetate) to give 620 mg (37%) of the title compound as a viscous oil. The product was homogeneous by TLC (ethyl acetate), and its structure was verified by 200 MHz NMR.

NMR (CDCl$_3$)δ:1.85–2.3 (m, 4H, cyclobutyl CH$_2$'s), 2.96, 3.17 (m, each 1H, cyclobutyl tertiary CH's), 4.27 (center of ABX octet, 2 H, NCH$_2$CH), 4.56 (center of ABX octet, 2H, CHCH$_2$OCO), 4.83 (broad s, 2H, NH$_2$), 5.55 (s, 2H, OCH$_2$Ar), 7.3–7.6 (m, 8H, ArH), 7.64 (s, 1H, ), 8.01 (d, J=8Hz, 2H, benzoyl ortho CH's).

From earlier chromatographic fractions was isolated a minor by-product, identified as 2-amino-6-benzyloxy-9-(p-toluenesulfonyl) purine. No N$^7$-alkylated product or other regioisomers were isolated.

EXAMPLE 5

2-Amino-9-[(2-benzyloxy-1,3,2-dioxaphosphorinan-5-yl) ethyl]-6-benzyloxypurine P-oxide 2-Amino-6-benzyloxypurine (113 mg from Example 1) was dissolved in sieve-dried DMF (1 ml) at 23° forming a cloudy solution. This solution was treated with a 57% sodium hydride oil dispersion (24 mg). After several minutes of vigorous magnetic stirring, the oily clumps of the reagent slowly broke up with effervescence, forming a cloudy solution. 2-Benzyloxy-5-(2'-p-toluenesulfonyl-oxyethyl)-2-oxo-1,3,2-dioxaphosphorinane (200 mg) was added to the reaction solution at 23° dissolving rapidly with magnetic stirring under dry nitrogen. After three hours, a sample of the solution was tested by thin layer chromatography on silica gel with ethyl acetate/10% methanol as the solvent.

The reaction was found to be incomplete and was therefore allowed to continue overnight. The reaction solution was then diluted with 25 ml of ethyl acetate, washed with four 5 ml portions of water, dried over magnesium sulfate, filtered, and evaporated at 60° under 0.1 mm pressure, leaving a colorless glass (254 mg). This material was subjected to preparative thin layer chromatography on 2000 micron silica gel plates, using chloroform/aqueous 90% methanol, 80/20, as the solvent, followed by further preparative thin layer chromatography on 500 micron plates using the same solvent. Extraction of the band having $R_f$0.47 with chloroform/aqueous 90% methanol, 80/20, filtration, and evaporation at about 60°, under 0.5 mm pressure, yielded the 7-isomer 5-[2'-(2-amino-6-benzyloxy-7H-purin-7-yl)ethyl]-2-benzyloxy-2-oxo-1,3,2-dioxaphosphorinane (46 mg):

NMR (CDCl$_3$)δ: 1.45 (m, 1H,$_H$$^{30}$ ); 2.08 (dt, 2H, J=7.5 and 7.5 Hz, —CH$_2$ $_H$+; 3.92 (m, 2H, J=20, (P), 11.5 (gem), <1 Hz, P—O—CH eq.); 4.15 (m, 2H, J=11.5 (gem), 4(P) <1 Hz, P—O—CH$_{ax}$); 4.20 (t, 2H, J=7.5 Hz, N-CH$_2$); 5.08 (d, 2H, J=8Hz, P—O—CH$_2$Ar); 5.26 (s, 2H, NH$_2$); 5.47 (s, 2H, —OCH$_2$Ar); 7.34–7.43 (m, 10H, Ar); 7.77 (s, 1H, C$_8$—H). A mass spectrum of the silylated product showed m/e of 567 (i.e. 495+72).

Extraction of the band having $R_f$=0.60 with chloroform/aqueous 90% methanol, 90/10, filtration, and evaporation at about 60°, under 0.5 mm pressure, yielded the 9-isomer 5-[2'-(2-amino-6-benzyloxy-9H-purin-9-yl)ethyl]-2-benzyloxy-2-oxo 1,3,2-dioxaphosphorinane (72 mg) as a colorless foam. Crystallization from ethanol gave colorless prisms, m.p. 162°-166°. A mass spectrum showed a molecular ion of 495.1663 (calculated was 495.1672).

NMR (CDCl$_3$)δ: 1.57 (m, 1H, $_H$+) 2.20 (dt, 2H, J=7 and 7Hz, CH$_2$+); 4.15 (t, 2H,'J=7Hz, N—CH$_2$); 4.18–4.32 (m, 4H, m, P(OCH$_2$)$_2$); 4.99(s, 2H, NH$_2$); 5.10 (d, 2H, J=8Hz, P—OCH$_2$Ar); 5.54 (s, 2H, OCH$_2$Ar); 7.29–7.52 (m, 10H, Ar); 7.59 (s, 1H, C$_8$—H).

Ultimate confirmation of structure was provided by single crystal X-ray crystallographic analysis, which showed the dioxaphosphorinane ring to be in the chair form, with the large 2,5-substituents trans and diaxial, and the attachment to the purine system to be at position 9.

EXAMPLE 6

(±)-2-Amino-6-benzyloxy-9-[(2,2-dimethyl-1,3-dioxolan-4-yl)propyl]purine

A solution of 2.41 g (10 mmole) of 2-amino-6-b.enzyloxypurine in 24 ml of dry DMF was treated with 0.44 g (11 mmole) of sodium hydride (60% dispersion in oil). The mixture was stirred under nitrogen as hydrogen was evolved. After gas evolution has ceased and a clear solution had formed a solution of 3.46 g (11 mmole) of (±)-2,2-dimethyl1,3-dioxalan-4-ylpropyl p-toluenesulfonate (prepared as above) in 2 ml of DMF was added. The mixture was stirred at 60° C. for 3 days. The cooled mixture was then neutralized with glacial acetic acid and concentrated in vacuo. The residue was taken up in ethyl acetate, filtered, re-concentrated and chromatographed on silica gel (elution with ethyl acetate). Evaporation of fractions containing clean product gave a residue which, on trituration with ether, yielded 975 mg (25%) of white crystals, m.p. 111°-112° C. The analytical batch, similarly prepared, had m.p. 115.5°-118° C.

Analysis Calculated for C$_{20}$H$_{25}$N$_5$O$_3$: C, 62.65; H, 6.57; N, 18.26; Found: C, 62.50; H, 6.49; N, 18.04;

EXAMPLE 7

2-amino-6-(o-nitrophenoxy)purine (2-Aminopurin-6-yl)trimethylammonium chloride (see Example 1, Step 1; 2.08 g, 9.10 mmol) and o-nitrophenol (2.45 g, 17.63 mmol) were suspended in dry dimethylsulfoxide (25 ml) and triethylamine (5.5 ml) was added. This mixture was stirred at 75° under a refux condenser under N$_2$ for 5½ hours, then left at room temperature overnight. The reaction mixture was poured into ice-1N HCl (300 ml) and the mixture was extracted with ethyl ether (3×300 ml). The aqueous layer was neutralized by careful addition of solid NaHCO$_3$ and then was extracted with ethyl acetate (3×300 ml). The organic phase was dried over MgSO$_4$, 1 filtered and evaporated to dryness to give a yellow solid. This material was dissolved in hot ethyl acetate purified by chromatography on silica gel, using ethanol-ethyl acetate (1:9) followed by ethanol-ethyl acetate (15:85) as developing solvents. Chromatographically and spectroscopically pure material was obtained in essentially quantitative yield.

EXAMPLE 8

2-Amino-9-(2-benzyloxy-1-ethoxymethyl)-6-(o-nitrophenoxy)purine

Method A

2-Amino-6-(o-nitrophenoxy)purine (275.6 mg, 1.01 mmol) was dissolved in dry DMF (5 ml) and 60% NaH in oil (66.1 mgs, 1.65 mmol of NaH) was added. The mixture was stirred under N$_2$ for 30 minutes and then 1-benzyloxy-2-chloromethoxy ethane (340 mg, 1.70 mmol) was added (washing-in with a little dry DMF). The reaction was stirred at room temperature overnight and then was poured into ice-H$_2$O (60 ml). This mixture was extracted with ethyl acetate (3×60 ml) and the pooled organic phrase was dried over MgSO$_4$, 1 filtered, and evaporated to dryness to give 670 mg of residue. This residue was dissolved in ethyl acetate and chromatographed on a silica gel 60 column packed in ethll acetate and then developed in ethanol-ethyl acetate (5:95). Fractions containing the required product were pooled and evaporated to dryness to give 190 mg (43% yield) of chromatographically and spectroscopically pure product.

Method B 2-Amino-6-(o-nitrophenoxy)purine (501 mg, 1.84 mmol) and hexamethyldisilazane (10 ml) were mixed and (NH$_4$)$_2$SO$_4$ (71.6 mg) was added. This mixture was heated under reflux for 3 hours, under N$_2$, and then evaporated to dryness in vacuo. The residue was dissolved in dry toluene (18 ml) and 9 ml of this solution (i.e. 0.92 mmol) was taken and Hg(CN)$_2$ (259.5 mg, 1.03 mmol) was added. This mixture was heated under reflux, under N$_2$, for 20 minutes and then 1-benzyloxy-2-chloromethoxyethane (230 mg, 1.15 mmol) was then added. The reflux under N$_2$ was continued for an additional 4 hours and then the mixture was left at room temperature overnight. The mixture was then poured into ethyl acetate (60 ml) and the organic phase was extracted successively with 30% aqueous KI solution (3×60 ml) and saturated NaCl solution (3×60 ml) before being dried (MgSO$_4$), filtered and evaporated to dryness to give 377 mg of residue. This material was dissolved in ethyl acetate and chromatographed on a silica gel column packed in ethyl acetate and developed in ethanol-ethyl acetate (5:95). Fractions containing the required product were pooled and evaporated to dryness to give 185.6 mg (46% yield) of material identical (as shown by chromatography and NMR) to that prepared by Method A.

EXAMPLE 9

2-Amino-6-(o-nitrophenoxy)-9-[(o-chlorophenoxy-1,3,2-dioxaphosphorinan-5-yl)oxy)methyl]purine P-oxide To 3.09 mmol of per-trimethylsilylated 2-amino-6-(o-nitrophenoxy) purine (prepared from 2-amino-6-(o-nitrophenoxy)purine and hexamethyldisilizane as described in Example 8, Method B) in sodium-dried toluene (4.5 ml) was added Hg(CN)$_2$ (850 mg, 3.37 mmol). This mixture was refluxed for 1 hour under N$_2$ and then 880 mg (2.81 mmol) of o-chlorophenoxy-2-oxo-1,3,2,-dioxaphosphorinan-5-yl chloromethyl ether (see Example 2) was added in 3 ml of dry toluene. This mixture was refluxed for 7 hours under N$_2$ and then allowed to stand at room temperature for 10 hours before being evaporated to dryness. The residue was triturated with CH$_2$Cl$_2$ (100 ml) and the organic phase was extracted successively with 30% aqueous KI solution (3×100 ml), 10% aqueous K$_2$CO$_3$ (3×100 ml) and H$_2$O (2×100 ml). The organic phase was dried over Na$_2$SO$_4$, filtered and then evaporated to dryness. This residue (740 mgs) was dissolved in a little CH$_2$Cl$_2$ and applied to a silica gel column packed in CH$_2$Cl$_2$. The column was developed with CH$_2$Cl$_2$, 2% MeOH in CH$_2$Cl$_2$ and then 3% methanol in CH$_2$Cl$_2$. The cis and trans isomers of the title compound (both N$^9$ substituted) could be separated by this column (172.5 mg of one isomer, 115.0 mg of the other, with 88.3 mg of a mixture of the two) and the total combined yield of material (cis and trans) was 375.8 mg (24%). Structures were verified by chromatography, mass spectroscopy, PMR and CMR. No N$^7$ isomers could be detected on any of the chromatograms.

EXAMPLE 10

2-Chloro-6-benzyloxypurine

Step 1: 2-Chloro-6-trimethylammonio-purinide[a]

2,6-Dichloropurine (40.01 g, 0.21 mol) was dissolved in glyme (400 ml) with warming. This solution was cooled to 0° and a solution of trimethylamine (about 250 ml, condensed at −78°) in glyme (250 ml) was added via a dropping funnel, under N$_2$, over a period of 2 to 3 minutes. The reaction was allowed to warm to room temperature, and was stirred overnight inder N$_2$. The precipitate which formed was filtered off and washed well with ethyl ether to give 61.4 g of chromatographically pure product. This material was triturated under ice-H$_2$O (500 ml), filtered and washed well with cold H$_2$O and then ethyl ether, before being dried in vacuo at room temperature. Yield 42.73 g (96%).

[a] preparation first described in J. Chem. Soc. (C), 1587 (1971).

Step 2: 2-Chloro-6-benzyloxypurine

Sodium spheres (250 mg, 10.87 mmol) and benzyl alcohol (2 ml, 19.33 mmol) were mixed and vigorously stirred under N$_2$ at 60°–100° (oil-bath) until all the sodium had dissolved (30 minutes) The mixture was cooled to room temperature and a suspension of 2-chloro-6-trimethylammoniopurinide (100 g, .73 mmol) in sieve-dried DMSO (10 ml) was added. This was stirred at room temperature under N$_2$ for 1¾ hours and the reaction mixture was then added dropwise to ice-H$_2$O (100 ml). The pH of the solution was adjusted to 7.0 using 1M HCl and the white solid which formed was filtered off, washing well on the pad with H$_2$O. This material was dried in vacuo over P$_2$O$_5$ at room temperature to give 0 mg (79.5% yield) of product. An analytical sample was obtained by recrystallizing from ethanol-H$_2$O and drying the product in vacuo. Analysis Calculated for:

C$_{12}$H$_9$N$_4$O$_1$Cl$_1$O 1H$_2$O: C, 54.91; H, 3.53; N, 21.35;Cl, 13.51; Found: C, 55.02; H, 3.49; N, 21.06; Cl; 13.52.

EXAMPLE 11

(S)-2-Chloro-6-benzyloxy-9(2,3-dibenzyloxy-1-propoxy-methyl)purine

2-Chloro-6-benzyloxypurine (782 mg, 3 mmol) was dissolved in sieve-dried DMF (10 ml) and 60% NaH in oil (160 mg; 4 mmol of NaH) was added. This mixture was stirred under $N_2$ for 20 minutes and then 963 mg (3 mmol) of (S)-2,3-dibenzyl-oxy-1-chloromethoxy propane (prepared from 1,2-di-O-benzyl-D-glycerol by chloromethylation with formaldehyde and HCl in methylene chloride at 0° C. using the method disclosed in European Patent Application No. 82401571.3, publication No. 0 074 306, or U.S. Ser. No. 617,868, filed June 6, 1984 in 10 ml of dry DMF was added. This mixture was stirred at room temperature under $N_2$ overnight after which time an additional 100 mg of (S)-2,3-dibenzyloxy-1-chloromethoxypropane was added. After 3 hours, the reaction was evaporated to dryness in vacuo, followed by an additional evaporation from toluene. The crude product was chromatographed on a column of Baker 3405 silica gel, developed first with ethyl ether and then with ethyl acetate. Fractions containing the required product were pooled and evaporated to dryness to give 970 mg (1.78 mmol, 59% yield) of pure material. 500 mg (0.92 mmol, 30.1% yield) of suspected $N^7$- isomer (NMR and mass spectroscopic identification) was obtained from later fractions, readily separated from the $N^9$ isomer.

EXAMPLE 12

2-Chloro-6-benzyloxy-9(1,3-dibenzyloxy-2-propoxymethyl) purine

2-Chloro-6-benzyloxypurine (1.56 g, 6 mmol) was dissolved in sieve-dried DMF (20 ml) and 60% NaH in oil (320 mg, 8 mmol of NaH) was added. This mixture was stirred under $N_2$ for 20 minutes and then 2.6 g (8 mmol) of 1,3-dibenzyloxy-2-chloromethoxypropane (W. T. Ashton, J. D. Karkas, A. K. Field and R. L. Tolman, Biochem Biophys Res. Comm. 108, 1716 (1982)) in 20 ml of dry DMF was added. This reaction was stirred overnight under $N_2$ and then evaporated to dryness in vacuo, followed by an additional evaporation from toluene. The crude product was chromatographed on a column of Baker 3405 silica gel, developed first with ethyl ether and then with ethyl acetate. Fractions containing the required product were pooled and evaporated to dryness to give 1.48 g (2.72 mmol, 45% yield) of pure material 1.09 g (2.0 mmol, 33% yield) of suspected $N^7$-isomer (NMR and mass spectroscopic identification) was obtained from later fractions, readily separated from the $N^9$-isomer

What is claimed is:

1. In a process for preparing 9-substituted-2,6-disubstituted purines comprising alkylation of a 9-substituted purine derivative, the improvement being the addition, prior to said alkylation, of a bulky, hydrophobic blocking group selected from the group consisting of 6-benzyloxy, substituted 6-benzxyloxy, 6-(2-phenylethoxy) and substituted 6-(2-phenyethoxy), wherein the substituents on the substituted 6-benzyloxy and 6-(2-phenylethoxy) are selected from $C_1$-to-$C_6$ alkyl, halo, nitro, phenyl and trifluoromethyl, to the 6-position of the purine and then the removal by standard methods, of said bulky, hydrophobic blocking grouop after said alkylation.

2. A process for preparing cyclic phosphates of 2,6-substituted purines comprising alkylating a purine having a blocking group selected from the group consisting of 6-benzyloxy, substituted 6-benzyloxy, 6-(2-phenylethoxy) and substituted 6-(2-phenylethoxy), wherein the substituents on the substituted 6-benzyloxy and 6-(2-phenylethoxy), arylsulfonyloxy, phenyl are selected from $C_1$-to-$C_6$ alkyl, halo, nitro, phenyl and trifluoromethyl, at the 6-position with a compound of the formula:

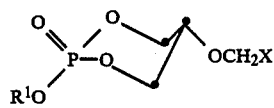

wherein $R^1$ is alkyl of 1 to 18 carbons, haloalkyl of 1 to 18 carbon atoms, benzyl substituted benzyl, phenyl or substituted phenyl, wherein halo means fluorine, chlorine, bromine or iodine and the substituents on the phenyl group or the phenyl moiety off the benzyl group are selected from $C_1$-$C_6$ alkyl, nitro and halogen; and X is a suitable leaving group selected from the group consisting of fluoride, choride, bromide, iodide and tosyloxy.

3. A process according to claim 2, wherein X is chloride and $R^1$ is O-chlorophenyl.

4. A process according to claim 2, wherein the purine is selected from 2-amino-6-benzyloxypurine, 2-amino-6-(o-nitrophenoxy)purine, 2-chloro-6-benzyloxypurine, 2-amino-6-chloropurine and 2,6-dichloropurine.

5. A process according to claim 1, wherein the 9-substituted purine derivative is selected from 2-amino-6-benzyloxypurine, 2-chloro-6-benzyloxypurine, 2-amino-6-(o-nitrophenoxy)purine, 2-amino-6-$\beta$-cyanoethoxy-purine, 2-amino-6-chloropurine and 2, 6-dichloropurine.

6. A process for preparing a compound of the formula

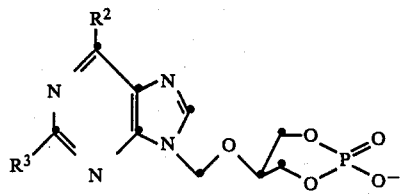

wherein $R^2$ is benzyloxy or o-nitrophenoxy; and $R^3$ is amino or chloro;

comprising alkylating a compound of the formula:

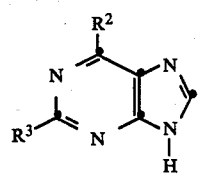

wherein $R^2$ and $R^3$ are as defined above with a compound of the formula:

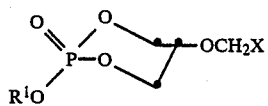

wherein R[1] is as defined above and X is a suitable leaving group selected from the group consisting of fluoride, chloride, bromide, iodide and tosyloxy.

7. A process according to claim 6, wherein X is chloride.

8. A process according to claim 1, wherein the purine or guanine has a blocking group selected from the group consisting of 6-benzylozy, substituted 6-benzxyloxy, 6-(2-phenylethoxy) and substituted 6-(2-phenylethoxy), wherein the substituents on the substituted 6-benzyloxy and 6-(2-phenylethoxy) are selected from $C_1$-to-$C_6$-alkyl, halo, nitro, phenyl and trifluoromethyl, at the 2 position also.

* * * * *